United States Patent [19]

Marquez et al.

[11] Patent Number: 5,324,831
[45] Date of Patent: Jun. 28, 1994

[54] PHOSPHORAMIDITE REAGENT FOR CHEMICAL SYNTHESIS OF MODIFIED DNA

[75] Inventors: Victor E. Marquez, Gaithersburg; Amanda J. Goddard, Silver Spring, both of Md.

[73] Assignee: The United States of America as represented by the Secretary of Health and Human Services, Washington, D.C.

[21] Appl. No.: 178,153

[22] Filed: Apr. 6, 1988

[51] Int. Cl.$^5$ ............................................. C07H 1/00
[52] U.S. Cl. ......................... 536/25.3; 536/25.34; 536/26.8
[58] Field of Search ................ 536/23, 27, 29, 28, 536/24, 25.3, 25.34, 26.8

[56] References Cited

U.S. PATENT DOCUMENTS

| | | | |
|---|---|---|---|
| 3,817,982 | 6/1975 | Verheyden et al. | 536/23 |
| 4,058,602 | 11/1977 | Beisler et al. | 536/23 |
| 4,458,066 | 7/1984 | Caruthers et al. | 536/27 |
| 4,668,777 | 5/1987 | Caruthers et al. | 536/27 |
| 4,843,066 | 6/1989 | Yamada et al. | 514/45 |
| 4,849,513 | 7/1989 | Smith et al. | 536/27 |

OTHER PUBLICATIONS

Tetrahedron, vol. 42, No. 2, pp. 501–513, 1986.
McBride et al., "Amidine Protecting Groups for Oligonucleotide Synthesis," J. Am. Chem. Soc., 1986, vol. 108, 2040–48.
Piskala et. al., "Nucleic Acids Components and their Analogues Synthesis of 1-Glycoxyl Derivatives of 5-azauracil and 5-azacytosine," Coll. Czech Chem. Comm., vol. 29, pp. 2060–2076 (1964).

*Primary Examiner*—John W. Rollins
*Assistant Examiner*—James O. Wilson
*Attorney, Agent, or Firm*—Morgan & Finnegan

[57] ABSTRACT

5,6-dihydro-5-azacytidine phosphoramidite is useful in the synthesis of oligonucleotides and DNA containing dihydro-5-aza- and 5-azacytosine bases. The modified oligonucleotides which contain 5-azacytosine residues at specific sites can be used to determine the mechanism of selective gene activation and the relationship existing between the presence of the triazine base and inhibition of DNA methylation.

5 Claims, 1 Drawing Sheet

FIG.1 Fragmentation pattern for dimer 12 obtained by negative ion FAB mass spectroscopy.

PHOSPHORAMIDITE REAGENT FOR CHEMICAL SYNTHESIS OF MODIFIED DNA

FIELD OF THE INVENTION

The present invention relates to the synthesis of DNA containing modified cytosine bases, namely 5-6-dihydro-5-azacytosine and 5-azacytosine, and more specifically to a reagent for use in the chemical synthesis of modified DNA which allows the incorporation of said bases at specific sites of a sequence.

BACKGROUND OF THE INVENTION

The ability to synthesize polynucleotide fragments having a desired nucleotide sequence is a useful tool in both research and applied molecular biology. Short synthetic polynucleotides, or oligonucleotides, are useful as adaptors or linkers in joining longer DNA segments, and as hybridization probes and DNA synthesis primers. Longer polynucleotides can be constructed from shorter segments having overlapping cohesive ends and used as structural genes, regulatory regions such as promoters, terminators, operators, and the like. It is thus of great interest to provide convenient automatic techniques for producing synthetic DNA fragments with high yields in a relatively short time.

As the understanding of the function, structure, and chemical makeup of nucleotide sequences, such as DNA, has evolved, so too has the awareness of the practicalities and feasibilities of genetic engineering. These engineering efforts, however, require a complete understanding of the chemical and biological reactions in cells. One of these reactions is the postreplicative modification of newly synthesized DNA by the selective methylation of certain cytosine residues which is performed enzymatically by a specific DNA methylase. An understanding of the factors governing the formation of specific methylation patterns in eucaryotic DNA is very important if we are to understand the mechanisms of gene expression.

Basic to such genetic engineering efforts is the synthesis of desired nucleotide chains from single mononucleotides. In this regard, electromechanical apparatus has been developed for synthesizing desired oligonucleotide sequences via the sequential linking of desired bases to a starting nucleotide.

At present, a variety of approaches for polynucleotide synthesis are available. These approaches can be characterized based on several criteria. First, the synthesis is usually carried out either on a solid-phase substrate or in solution. Solid-phase synthesis relies on sequential addition of mononucleotides to a growing chain attached at one end to the substrate. The solid phase permits easy separation of the reactants, but the method requires excess quantities of reactants and usually provides only small quantities (less than 1 mg) of the desired sequence. Solution phase synthesis, while it requires lesser amounts of the expensive reagents and can provide larger quantities of the product sequence, requires isolation and purification of the intermediate product after every addition. Virtually all automated polynucleotide systems rely on solid phase synthesis.

There are presently two synthesis chemistries in widespread used for automated polynucleotide synthesis. The triester method, as described by Catlin and Cramer *J. Org. Chem.* 38: 245-250 (1973) and Itakura et al., *Can. J. Chem.* 51: 3649-3651 (1973) which relies on the addition of suitable blocked phosphate-triester intermediates which are generally inexpensive and stable. The phosphite-triester method, as described by Letsinger and Lunsford in *J. Am. Chem. Soc.* 98:3655 (1975) is somewhat more complex, but generally provides higher yields than the phosphate triester method. The utility of the phosphite-triester method was greatly improved by the use of N,N-dialkylamino phosphites (amidites) which are more stable than the phosphorchlorodite intermediates initially employed. While the phosphite-triester method is often favored because of the greater yield at each nucleotide addition, the phosphate-triester method is also suitable for automated polynucleotide synthesis.

Among the reactor systems that can be used in synthesizing polynucleotides are solid-phase reactor systems which use either a tight bed column, a loose bed column, or a batch reactor. The tight bed column is tightly packed with the solid-phase support and the reactants are introduced either in a single pass or by a recirculating stream.

Loose bed columns have been introduced to alleviate these problems partially. By slowly passing the reactant through the column, higher mass transfer rates are achieved and utilization of the expensive reactants is improved. Also, channelling is reduced, since the solid phase packing will shift to equalize the flow profile therethrough.

In a batch reactor, the support matrix is held in an enclosed vessel. Reactants are introduced and the vessel contents agitated, typically by bubbling an inert gas through the liquid in the reactor. While such a system can provide very efficient utilization of the reactants by increasing the retention time in the reactor, relatively large volumes of the reactant and solvent are necessary to fill the reactor.

Urdea et al., in U.S. Pat. No. 4,517,338, disclose a method and system for sequential modification of a linear polymeric molecule attached to a dispersed solid phase support by adding individual nucleotides in a predetermined order to a nucleotide chain. The dispersed solid phase is retained within a reactor zone which is provided with access ports for the introduction and removal of reagents. Reagents are selectively delivered to the reactor zone through at least one of the access ports by a reagent manifold.

Another apparatus for programmably synthesizing selected nucleotide sequences is described in Zelinka et al., U.S. Pat. No. 4,598,049.

The well known instability of the triazine ring of 5-azacytosine deoxyribonucleoside makes it unsuitable for use as a building block in the aforementioned automated DNA syntheses. Despite this drawback, interest in the synthesis of single and double stranded DNA fragments containing 5-azacytosine residues constitutes an important goal in the understanding of the mechanism of action of this drug. DNA incorporation of 5-azacytosine in living cells has been associated with inhibition of DNA methylase activity and consequent gene activation.

Because of the well established relationship that exists between the DNA incorporation of 5-azacytosine residues and gene activation, it would be o useful to develop a methodology for the synthesis of oliqonucleotide fragments which contain this unnatural base. These modified oligonucleotides, which would contain 5,6-dihydro-5-azacytosine and 5-azacytosine residues at specific sites, could serve as tools for elucidating the mechanism of selective gene activation and the relationship that exists between the presence of these triazine bases and inhibition of DNA methylation. A direct incorporation of the phosphoramidite of 2'-deoxy-5-aza-cytidine in DNA synthesis would results in failure, since the 2'-deoxy-5-aza-cytidine is extremely sensitive to acid or alkaline conditions.

SUMMARY OF THE INVENTION

It is an object of the present invention to overcome deficiencies in the prior art, such as noted above.

It is a further object of the invention to provide a method for the synthesis of modified oligonucleotides containing either 5,6-dihydro-5-azacytosine or 5-azacytosine bases at specific sites of the sequence.

It is another object of the present invention to provide a reagent for the automated synthesis of DNA to accomplish the incorporation of 5,6-dihydro-5-azacytosine and 5-azacytosine bases.

It is also an object of the present invention to provide for a method of converting 5,6-dihydro-5azacytosine to 5-azacytosine in an oligonucleotide structure.

It is yet a further object of the present invention to provide compounds for use in studying the mechanism of selective gene activation.

The use of a phosphoramidite of 2'-deoxy-dihydro-5-aza-cytidine in DNA synthesis results in the successful formation of the desired internucleotide linkage and permits the synthesis of modified DNA fragments, since it is totally compatible with all of the chemical steps used in DNA synthesis. At the conclusion of the synthesis, a very specific and easily performed oxidation generates the desired 5-aza-cytosine moiety. Since the hydrolytic instability of the triazine ring in 5-azacytosine nucleosides is very well documented, the use of a conventional phosphoramidite derivative of 5-azacytosinedeoxyribose, compound 1, is impractical, as this would have resulted in the basecatalyzed cleavage of the triazine ring during the last deprotection step of the synthesis. The process of the present invention overcomes this problem by using a stable phosphoramidite precursor of 5-azacytosinedeoxyribose that permits regeneration of the desired 5-azacytosine base after the conclusion of the synthesis of the oligonucleotide.

The protected 5,6-dihydro-5-azacytidine phosphoramidite, compound 9, has a very stable triazine ring, analogous to its parent nucleoside.

The reactions according to the present invention are shown in the following reaction schemes:

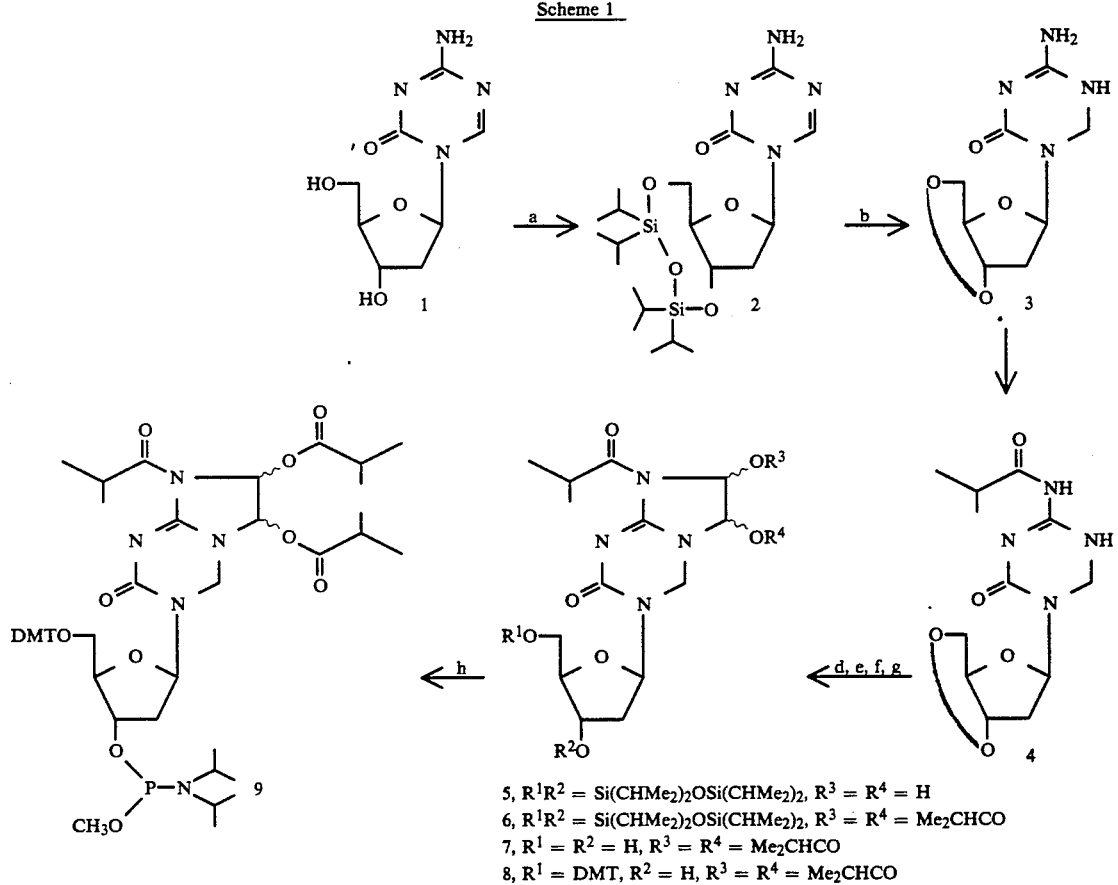

Scheme 1

5, $R^1R^2$ = Si(CHMe$_2$)$_2$OSi(CHMe$_2$)$_2$, $R^3$ = $R^4$ = H
6, $R^1R^2$ = Si(CHMe$_2$)$_2$OSi(CHMe$_2$)$_2$, $R^3$ = $R^4$ = Me$_2$CHCO
7, $R^1$ = $R^2$ = H, $R^3$ = $R^4$ = Me$_2$CHCO
8, $R^1$ = DMT, $R^2$ = H, $R^3$ = $R^4$ = Me$_2$CHCO a) 2.2 eq. 1,3-dichloro-1,1,3,3-tetraisopropyldisiloxane, pyridine, rt, 1 h, 97%.
b) 8 eq. NaBH$_4$, THF, rt, 1 h, 78%.
c) i. 6 eq. isobutyryl chloride, pyridine/chloroform, 0°, ii, MeOH, rt, 16 h, 84%.
d) i. 40 eq. glyoxal, pyridine, rt, thrice reduced to dryness, ii. chloroform/water extraction.
e) 2 eq. isobutyryl chloride, pyridine, rt, 2 h, 61%.
f) 1.2 eq. tetrabutylammonium fluoride, THF, rt, ½ h, 60%.
g) 1.2 eq. 4,4'-dimethoxytrityl chloride, pyridine, rt, 2 h, 50%.
h) 2.2 eq. chloro-N,N-diisopropylamino methoxyphosphine, 4.2 eq. tetrazole, chloroform, rt, 15 min, 71%.

Scheme 1 outlines the synthesis of 5-azacytidine phosphoramidite starting with 5-azacytosinedeoxyribose. Protection with 1,3-dichloro-1,1,3,3-tetraisopropyldisiloxane, followed by borohydride reduction of compound 2, gave the desired dihydro analog, compound 3, after purification by silica gel flash chromatography with 5% methanol in ethyl acetate. The $^1$H-NMR spectrum of compound 3 shows the newly generated C-6 methylene protons as an AB quartet centered at 4.40 ppm. The exocyclic amino group of compound 3 was then protected as the isobutyrylamide, compound 4, and purified by silica gel flash chromatography with 50% ethyl acetate in hexane. Complete protection of the triazine ring was accomplished with the introduction of the bis(isobutyryloxy)ethylene group, performed in the same manner as for 2'-deoxyguanosine. Thus, the intermediate diol, compound 5, isolated from the reaction of compound 4 with glyoxal, was reacted with isobutyryl chloride to give compound 6, which was purified by silica gel flash chromatography with 15% ethyl acetate in hexane. Removal of the tetraisopropyldisiloxane group in compound 6 with tetrabutylammonium fluoride gave compound 7, following a simple extraction in methylene chloride/water. Protection of the 5'-hydroxyl group was accomplished by the standard procedure using 4,4'-dimethoxytrityl chloride to yield compound 8 as a crystalline solid, mp 89°–91° C. (hexane). Finally, phosphitylation of compound 8 with chloro-N,N'-diisopropylaminomethoxyphosphite gave the desired phosphoramidite, compound 9, as a white solid, mp 67°–69° C. after purification by silica gel flash chromatography with 25% ethyl acetate in hexane.

The reactivity of the new phosphoramidite, compound 9, was initially tested under the standard conditions used for DNA synthesis in a typical tetrazole-catalyzed condensation reaction with 3'-O-acetyl-thymidine, as shown in Scheme 2. After 15 minutes, the reaction was complete, and was immediately oxidized in situ to give a quantitative yield of the fully protected dimer, compound 11. Removal of the dimethoxytrityl group with trichloroacetic acid and further treatment of the residue with concentrated ammonium hydroxide yielded the fully blocked dimer, compound 12

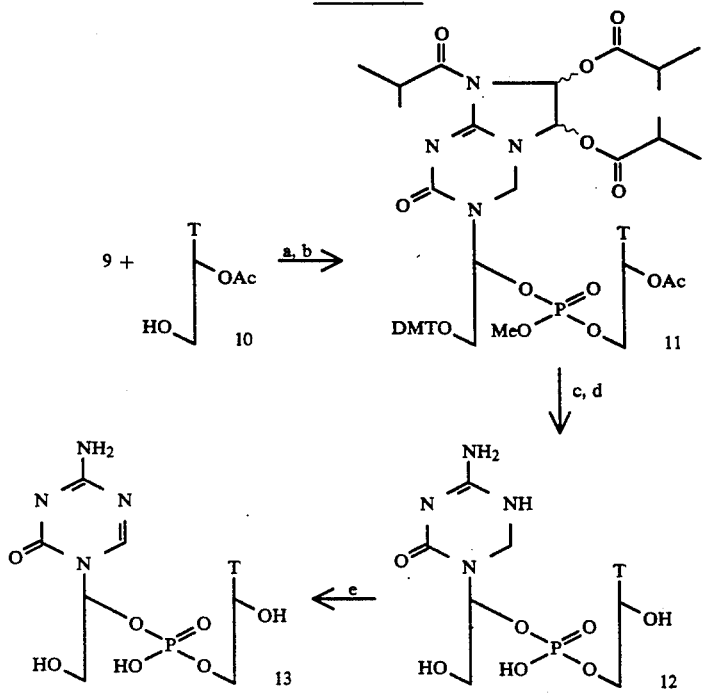

Scheme 2 a) 1.5 eq phosphoramidite 9. 5 eq tetrazole, MeCN, rt, 15 min.
b) Iodine, 3%; water, 2%; 2,6-lutidine, 2%, THF, 93%; rt, 10 min.
c) trichloroacetic acid, 2% in dichloromethane, rt, 10 min.
d) conc. NH$_4$OH, 50°, 15 h.
e) i. 250 eq bis(trimethylsilyl)-trifluoroacetamide, MeCN, reflux, 1 h, ii. 50% methanol in water, rt, 1 h.

In order to test the new reagent, two decamers in which the cytosine base at positions 3 and 6 was replaced by the 5,6-dihydro-5-azacytosine moiety, were synthesized in an Applied Biosystems model 380A automated DNA synthesizer. Based on the trityl assay data, the stepwise yield was 98.5% and 98.4%, respectively, compared to 99.09% for the unmodified decamer.

The final conversion of the dihydrotriazine base to the aromatic triazine was successfully accomplished by the use of bis(trimethylsilyl)trifluoroacetamide (BSTFA) and trimethylsilyl chloride as silylating reagents, and trimethylsilyl peroxide as an oxidizing reagent. For the transformation the dimeric compound 12 was used as a model and the resulting dimer 13 was prepared in quantiative yield.

BRIEF DESCRIPTION OF THE DRAWINGS

FIG. 1 shows the fragmentation pattern for dimer 12 obtained by negative ion FAB mass spectroscopy

Figure 2:
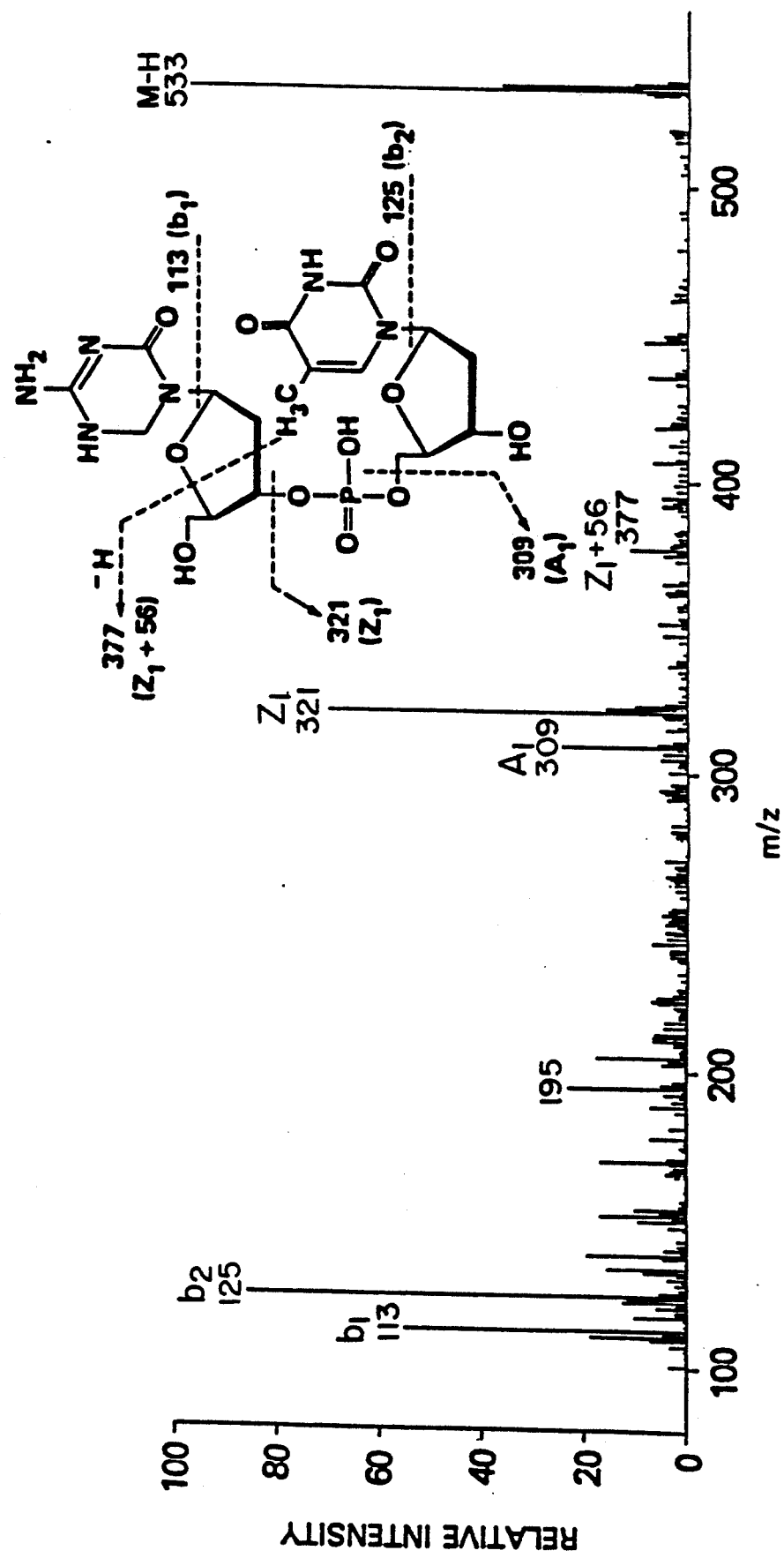
FIG. 2 shows autoradiography of synthetic oligonucleotides obtained after 5'-end labelling and polyacrylamide gel electrophoresis.

Lane 1: (CA)3, hexamer marker
Lane 2, (AT)4, octamer marker
Lane 3, TACGTCGCAG, patent decamer Lane 4, TAXGTCGCAG, 3-modified decamer
Lane 5, TACGTXGCAG, 6-modified decamer
X=5,6-dihydro-5-azacytidine.
DETAILED DESCRIPTION OF THE INVENTION
The detailed reaction schemes are shown as follows:
Scheme 3
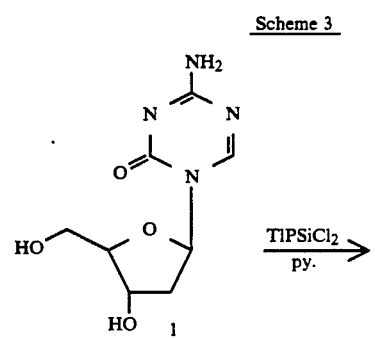
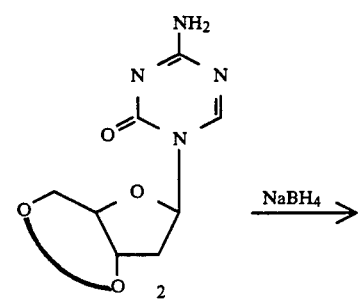
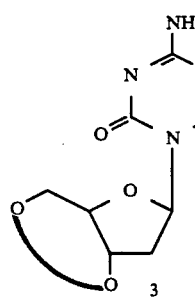
Scheme 4
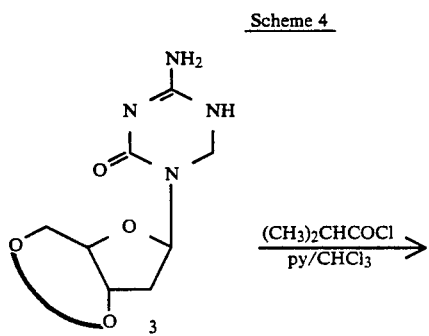
-continued
Scheme 4
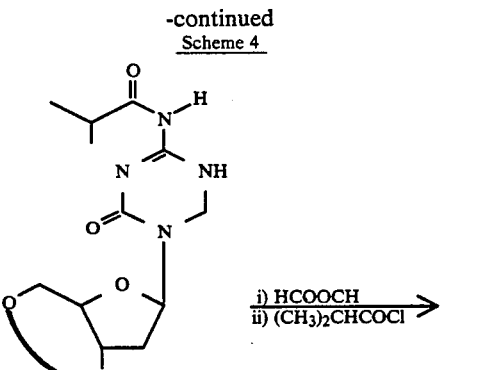
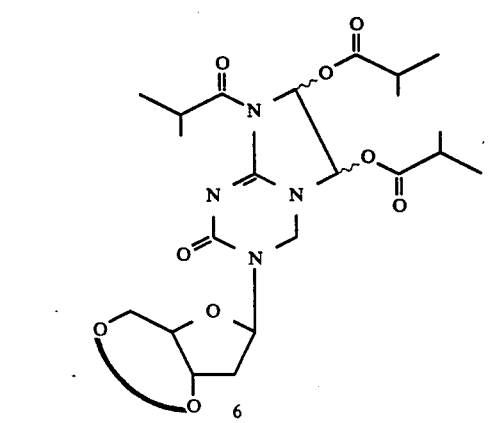
Scheme 5
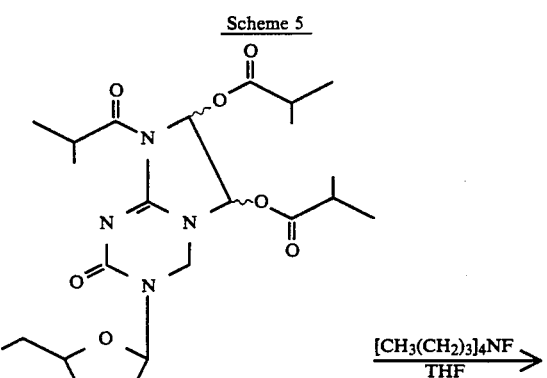
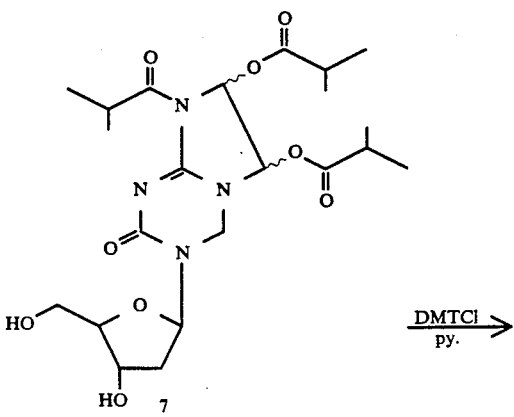

-continued
Scheme 5
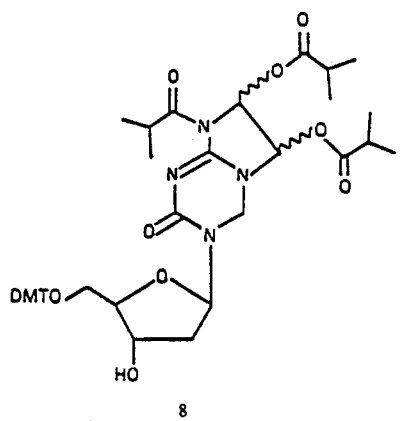
8
Scheme 6
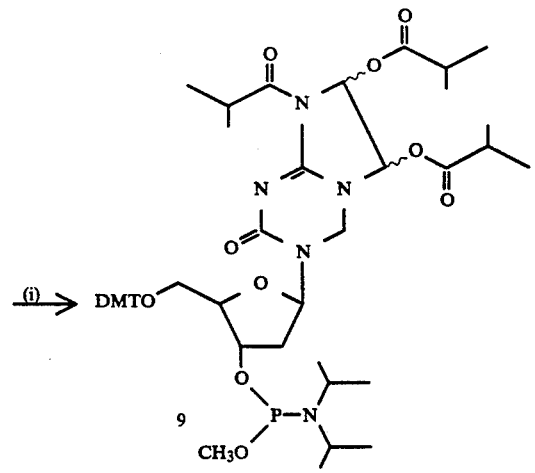
i) CH₃OP(Cl)N[CH(CH₃)₂]₂; [(CH₃)₂CH]₂NCH₂CH₃; CH₂Cl₂
³¹P NMR   149.07
          148.97
          148.56
          148.48

Scheme 7
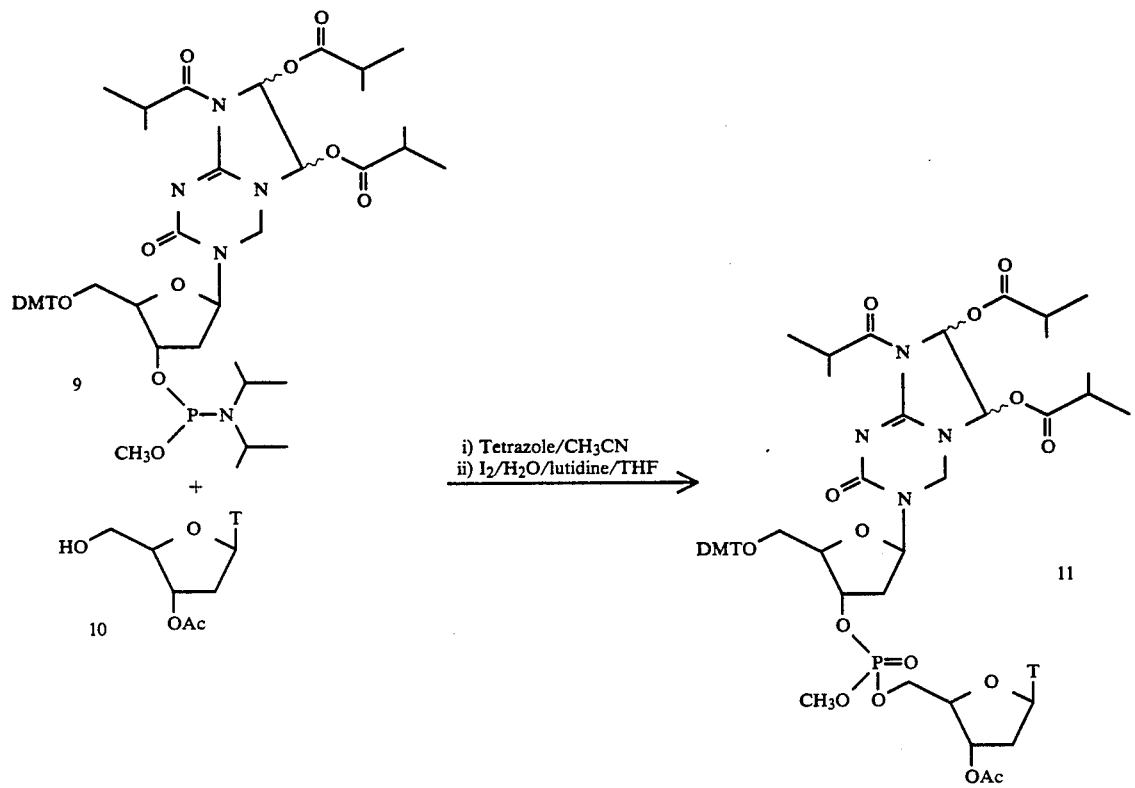
Scheme 8
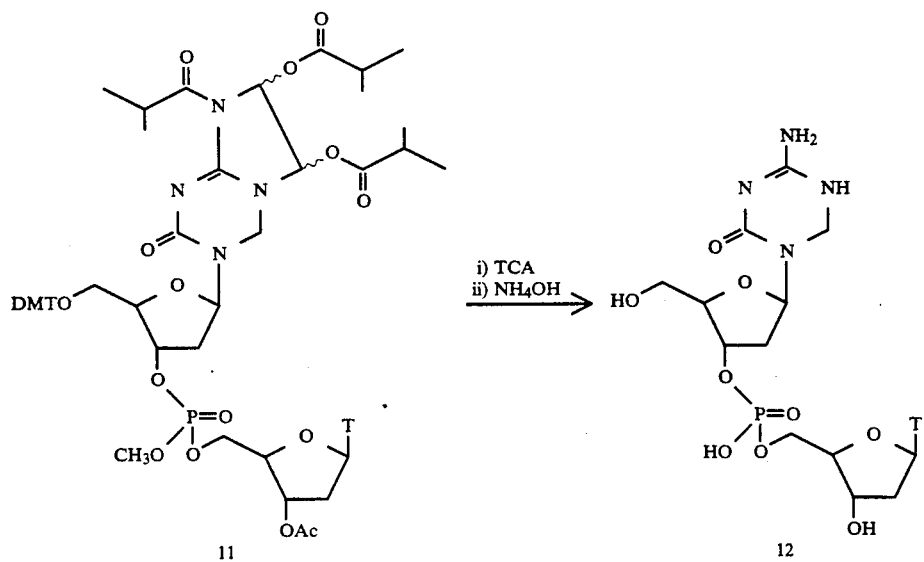

Scheme 9

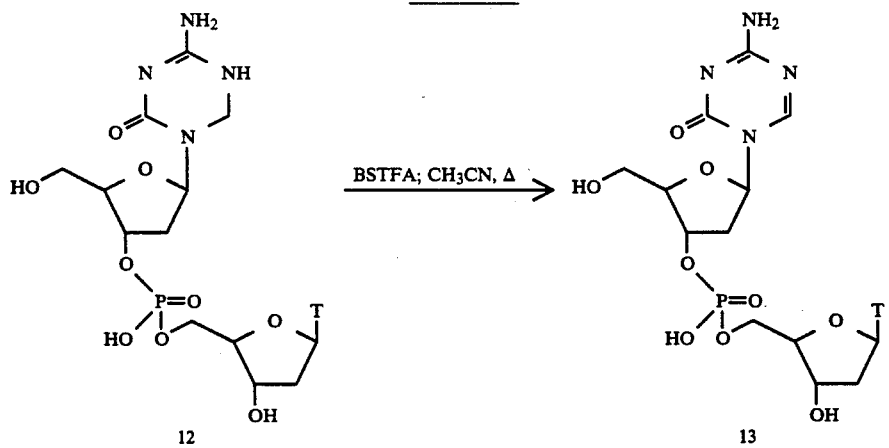

The synthesis of phosphoramidite according to the present invention started with 2'-deoxy-5-azacytidine, compound 1. As shown in Scheme 3, the 3' and 5' hydroxy groups were simultaneously protected with 1,3-dichloro-1,1,3,3-tetraisopropyldisiloxane using pyridine as solvent and base, according to the procedure of Markiewick et al. in *Bull. Pol. Acad. Sci.*, 32: 433, 1984. This reaction proceeded in 97% yield, giving the desired compound 3 as a foam. In this and the following schemes, the tetraisopropyldisiloxane group is depicted as a semicircle joining the 3' and 5' oxygen atoms of the nucleoside.

In the subsequent step, shown in Scheme 3, the double bond was reduced either catalytically with hydrogen over palladium on carbon, or more efficiently with sodium borohydride in tetrahydrofuran. After one hour of reaction, followed by treatment with methanol and water, workup and chromatography over silica gel with 5% methanol in ethyl acetate, the desired product, compound 4, was obtained in 78% yield as a foam.

Referring to Scheme 4, the exocyclic amino function was protected at this point in 84% yield by treatment of compound 3 with isobutyryl chloride in pyridine. After a conventional workup and silica gel chromatography with 50% hexane in ethyl acetate, compound 4 was obtained as a foam.

As shown in Scheme 4, complete protection of the aglycon moiety was achieved by introducing the isobutyryloxyethylene group. Reaction of compound 4 with glyoxal, followed by treatment of the cyclized intermediate with isobutyrl chloride in anhydrous pyridine, gave compound 6 after purification by silica gel column chromatography with 15% ethyl acetate in hexane. Compound 6 was isolated as a foam in 61% yield.

Referring to Scheme 5, compound 7 was prepared by removing the sugar tetraisopropyldisiloxane protective group with tetrabutylammonium fluoride at room temperature in THF. This compound was purified by simple extraction in methylene chloride after the reaction mixture was reduced to dryness and partitioned between water and methylene chloride to give compound 7 as a foam in 59% yield.

Selective protection of the 5'-hydroxy group, as required for DNA synthesis, was accomplished by the standard procedure using 4,4'-dimethoxytrityl chloride in dry pyridine to yield compound 8 is 50% yield as crystalline solid, mp 89°–91° C.

Scheme 6 shows the phosphitylation of compound 8 in the presence of diisopropylamine in methylene chloride with chloro(diisopropylamino)methoxy phosphine to give 71% yield of compound 9 as a glassy substance after purification by silica gel column chromatography with 25% ethyl acetate in hexane.

The phosphoramidite of the present invention, compound 9, is used in a typical condensation reaction to synthesize DNA. The phosphoramidite was mixed with 3'-O-acetyl thymidine, compound 10, as shown in Scheme 7, in acetonitrile in the presence of tetrazole as the condensing catalyst, according to the procedure of Pfleiderer and Schwarz (*Tetrahedron Letters*, 25: 5513, 1984). Thin layer chromatography showed complete reaction after fifteen minutes, and the dimeric product was immediately oxidized in situ with a mixture of iodine, lutidine, THF, and water to give a quantative yield of the fully protected dimer phosphate, compound 11. Treatment of a solution of this dimer in dichloromethane with trichloroacetic acid removed the dimethoxytrityl group, and treatment of the residue with concentrated ammonium hydroxide at 55° C. for fifteen hour yielded the fully deblocked target dimer, as shown in Scheme 8. An analytical sample of the deblocked dimer was obtained after reversed phase chromatography on J. T. Baker C-18 silical gel, 40 micrometers, 5% methanol in water, and as shown in FIG. 1, the FAB/MS was consistent with the expected structure.

Finally, the dihydro-5-azacytidine containing dimer, compound 12, was suspended in dry acetonitrile and treated with an excess of bis(trimethylsilyl)trifluoroacetamide, trimethylsilyl chloride, and trimethylsilylperoxide under reflux overnight, as shown in Scheme 9. Oxidation to the 5-azacytidine stage took place quantitatively as assessed by the dominance of the M-H peak in the mass spectrometer at m/z 531. The workup was very simple and involved evaporation of the volatile solvent and reagent and treatment of the residue with water to deblock the remaining oxygen and nitrogen to silicon linkages. Lyophilization of the aqueous solution yielded the desired dimer, compound 13.

In order to test the utility of the new regent, two decamers, shown in FIG. 2, lanes 4 and 5, in which the cytosine base at positions 3 and 6 was replaced by the 5,6-dihydro-5-azacytosine moiety, were synthesized in an Applied Biosystems model 380A automated DNA synthesizer. Based on the trityl assay data, the stepwise yield was 98.5% and 98.4%, respectively, compared to 99.09% for the unmodified decamer (FIG. 2, lane 3).

While the invention is described above in relation to certain specific embodiments, it will be understood that many variations are possible, and that alternative materials and reagents can be used without departing from the invention. In some cases such variations and substitutions may require some experimentation, but such will only involve routine testing.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. 5,6-dihydro-5-azacytidine phosphoramidite.

2. 5,6-dihydro-5-azacytidine phosphoramidite with protecting groups on the amino groups of the azacytidine ring and on the 5' hydroxy group, wherein said protecting groups are suitable for use in the phosphoramidite synthesis of polynucleotides.

3. A compound selected from the group consisting of:

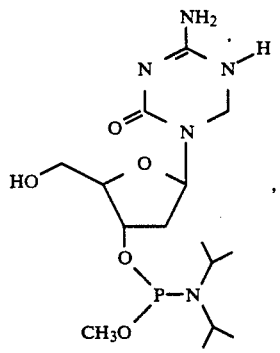

,

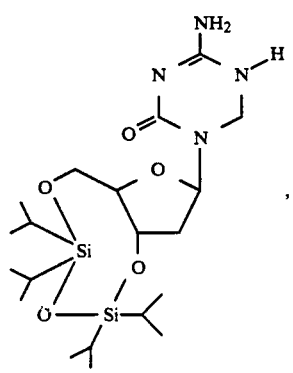

,

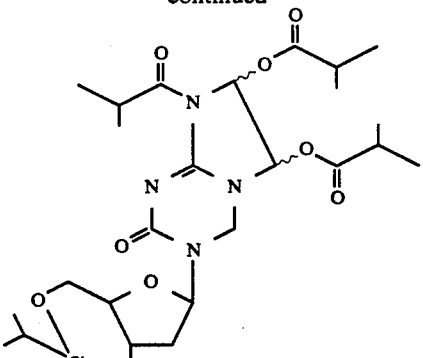

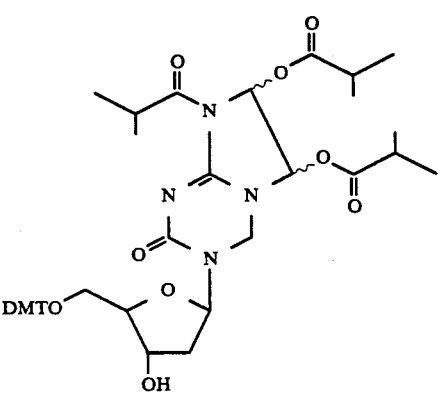

and

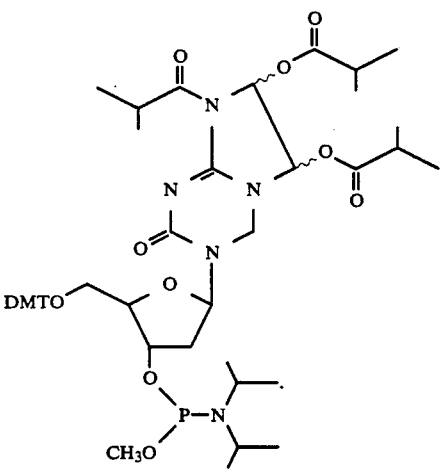

4. In a method for synthesizing a polynucleotide containing at least one modified cytosine base using the phosphoramidite method, wherein the improvement in said method is that the modified cytosine base is 5-azacytidine and the polynucleotide is prepared by:

a) using the phosphoramidite method to synthesize a polynucleotide containing at least one 5,6-dihydro-5-azacytidine base;

b) and selectively oxidizing said 5,6-dihydro-5-azacytidine base in the polynucleotide formed in step a) to a 5-azacytidine base.

5. The process of claim 4, wherein said selective oxidizing of step b) is carried out with bis(trimethylsilyl)-trifluoroacetamide, trimethylsilyl chloride and trimethylsilyl peroxide.

* * * * *